(12) United States Patent
Haft

(10) Patent No.: US 9,778,142 B2
(45) Date of Patent: Oct. 3, 2017

(54) METHOD FOR DETECTING FUEL DISCHARGE FROM THE OIL

(71) Applicant: Continental Automotive GmbH, Hannover (DE)

(72) Inventor: Gerhard Haft, Lappersdorf (DE)

(73) Assignee: CONTINENTAL AUTOMOTIVE GMBH, Hannover (DE)

( * ) Notice: Subject to any disclaimer, the term of this patent is extended or adjusted under 35 U.S.C. 154(b) by 266 days.

(21) Appl. No.: 14/435,824

(22) PCT Filed: Oct. 10, 2013

(86) PCT No.: PCT/EP2013/071156
§ 371 (c)(1),
(2) Date: Apr. 15, 2015

(87) PCT Pub. No.: WO2014/060283
PCT Pub. Date: Apr. 24, 2014

(65) Prior Publication Data
US 2015/0292983 A1      Oct. 15, 2015

(30) Foreign Application Priority Data
Oct. 15, 2012   (DE) .................. 10 2012 218 759

(51) Int. Cl.
*G01M 15/10* (2006.01)
*F02D 41/14* (2006.01)
(Continued)

(52) U.S. Cl.
CPC ....... *G01M 15/104* (2013.01); *F02D 41/1454* (2013.01); *G01N 33/2835* (2013.01);
(Continued)

(58) Field of Classification Search
CPC .................................. G01M 15/104
See application file for complete search history.

(56) References Cited

U.S. PATENT DOCUMENTS

| 7,996,141 B2 | 8/2011 | Pache et al. | 701/103 |
| 8,046,153 B2 | 10/2011 | Kurtz et al. | 701/103 |

(Continued)

FOREIGN PATENT DOCUMENTS

| CN | 102337975 A | 2/2012 | F02D 19/08 |
| DE | 10222808 A1 | 11/2003 | F02D 41/00 |

(Continued)

OTHER PUBLICATIONS

International Search Report and Written Opinion, Application No. PCT/EP2013/071156, 20 pages Apr. 1, 2014.

(Continued)

*Primary Examiner* — Peter Macchiarolo
*Assistant Examiner* — Timothy Graves
(74) *Attorney, Agent, or Firm* — Slayden Grubert Beard PLLC

(57) ABSTRACT

A method is provided for detecting fuel discharge from a lubricant in a housing of an internal combustion engine. A first lambda deviation is measured by a lambda sensor for a first mass air flow supplied in an intake tract of the engine. A second lambda deviation is measured by the lambda sensor for a second mass air flow that differs from the first mass air flow, and is supplied in an intake tract of the engine. An actual comparative value is calculated from the measured first and second lambda deviations. A desired comparative value indicative of the fuel discharge is calculated from a first desired lambda deviation for the first mass air flow, and a second desired lambda deviation is calculated for the second mass air flow. The fuel discharge is detected based on a comparison of the actual comparative value and the desired comparative value.

10 Claims, 2 Drawing Sheets

(51) Int. Cl.
*G01N 33/28* (2006.01)
*F02D 41/08* (2006.01)
*F02D 41/00* (2006.01)

(52) U.S. Cl.
CPC .......... *F02D 41/0025* (2013.01); *F02D 41/08* (2013.01); *F02D 2250/08* (2013.01); *F02D 2250/11* (2013.01)

(56) References Cited

U.S. PATENT DOCUMENTS

| | | | | |
|---|---|---|---|---|
| 8,161,952 | B2 | 4/2012 | Satou | ............................ 123/572 |
| 8,332,123 | B2 | 12/2012 | Miersch-Wiemers et al. | ............................ 701/102 |
| 2002/0139360 | A1* | 10/2002 | Sato | ................... F02D 41/0037 123/698 |
| 2009/0088949 | A1* | 4/2009 | Pache | ................. F01M 13/022 701/103 |
| 2009/0133678 | A1 | 5/2009 | Mallebrein et al. | .......... 123/679 |
| 2010/0070152 | A1* | 3/2010 | Miersch-Wiemers | ............................. F02D 41/047 701/102 |
| 2012/0310514 | A1 | 12/2012 | Viehöver et al. | ............. 701/112 |
| 2013/0174800 | A1* | 7/2013 | Malm | ..................... F02B 75/00 123/1 A |
| 2013/0297184 | A1 | 11/2013 | Nilsson et al. | ............... 701/103 |

FOREIGN PATENT DOCUMENTS

| | | | | |
|---|---|---|---|---|
| DE | 102006059675 A1 | 6/2008 | ............. | F01M 11/10 |
| DE | 102007046489 B3 | 5/2009 | ............. | F02D 45/00 |
| DE | 102009001619 A1 | 10/2009 | ............. | F02D 43/00 |
| DE | 102010006580 B3 | 7/2011 | ............. | F02D 41/00 |
| DE | 102010043780 A1 | 5/2012 | ............. | F01M 13/02 |
| WO | 2014/060283 A1 | 4/2014 | ............. | F02D 41/14 |

OTHER PUBLICATIONS

Chinese Office Action, Application No. 201380053943.4, 13 pages Aug. 18, 2016.

* cited by examiner

FIG. 2

Method

- Measure a first lambda deviation during a first air mass flow
- Measure a second lambda deviation during a second air mass flow
- Determine an actual comparison value from the deviations
- Determine a setpoint comparison value based on the air mass flows
- Detect a fuel discharge from a lubricant by comparing the actual comparison value to the setpoint comparison value
- Adjust the injected fuel quantity based on the detected fuel discharge

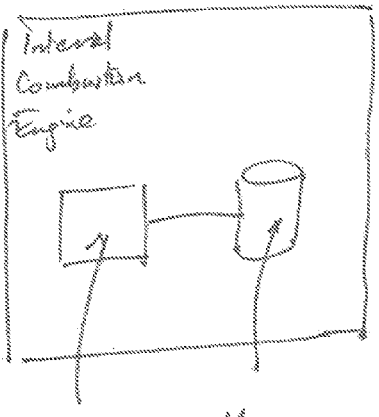

FIG. 3

Internal Combustion Engine

Processor   Memory

METHOD FOR DETECTING FUEL DISCHARGE FROM THE OIL

CROSS-REFERENCE TO RELATED APPLICATIONS

This application is a U.S. National Stage Application of International Application No. PCT/EP2013/071156 filed Oct. 10, 2013, which designates the United States of America, and claims priority to DE Application No. 10 2012 218 759.6 filed Oct. 15, 2012, the contents of which are hereby incorporated by reference in their entirety.

TECHNICAL FIELD

The present invention relates to a method for detecting fuel discharge from a lubricant in a housing of an internal combustion engine of a motor vehicle. In addition, the present invention relates to a control unit for an internal combustion engine of a motor vehicle.

BACKGROUND

In the case of a cold start and in the case of warm running of a spark-ignition engine, in some cases considerable quantities of fuel are input in an engine oil in the crank casing. During a further course of the heating up of the spark-ignition engine this fuel vaporizes out of the engine oil, for example at relatively high engine temperatures, and is discharged into an intake manifold of the spark-ignition engine via a crank casing venting system. A desired fuel/air mixture is fed to the cylinders of the spark-ignition engine through the intake manifold. The additional introduction of the vaporized fuel from the crank casing into the intake manifold causes the fuel/air mixture in the intake manifold to be enriched. This additional fuel in the intake manifold can in extreme cases, in particular when ethanol-containing fuels are used, bring about massive over-enrichment of the fuel/air mixture and therefore over-enrichment of the spark-ignition engine.

Over-enrichment is usually compensated by a Lambda controller. The Lambda controller is a sensor which measures the respective residual oxygen content in the combustion discharge gas of the spark-ignition engine, in order to be able to regulate on the basis thereof the ratio of the combustion air to fuel for the rest of the combustion, in such a way that, for example, neither an excess of fuel nor an excess of air occurs. If, for example, unburnt fuel in the combustion discharge gas is measured, the fuel/air mixture is set to be leaner in the intake section. The objective is to generate, as a function of the fuel used, a lambda value of $\lambda \approx 1$ in the fuel discharge gas, without severe deviations occurring therefrom.

Correspondingly measured lambda deviations are used, for example, for diagnostic purposes (what is referred to as fuel system diagnosis FSD) and for detection of the proportion of ethanol in the fuel. If a lambda deviation occurs which arises as a result of the outgased fuel which is fed into the intake section, incorrect error detection of the diagnosis or an incorrectly measured ethanol proportion value can be caused. It is therefore important to detect whether the lambda deviation has been caused by fuel discharge from the engine oil or, for example, by a defect in the spark-ignition engine itself.

Previously, in order to detect possible fuel discharge from an engine oil, what are referred to as fuel input/discharge models in engine control were calculated and compared with different operating conditions of the engine. Since the fuel input/discharge depends very greatly, inter alia, on the fuel used (fuel quality, ethanol proportion), such fuel input/discharge models can only make a statement as to whether fuel discharge from the engine oil is theoretically possible. If the spark-ignition engine is running under operating conditions in which, according to the calculated oil input/discharge model, it is possible for fuel to be discharged, the diagnoses described above, ethanol proportion detection processes or lambda adaptations are disabled in order to prevent any incorrect measurements being obtained. The actual quantity of fuel discharge can as a result be estimated only coarsely. Such detection of the fuel discharge by means of fuel input/discharge models can also be achieved only at very high cost.

Alternatively, what is referred to as a HC sensor (hydrocarbon sensor) can be installed in the crank casing venting means. The HC sensor can measure the proportion of the hydrocarbons from the fluid vented from the crank casing. However, such HC sensors are expensive and therefore tend not to be very suitable for use in series fabrication.

SUMMARY

One embodiment provides a method for detecting fuel discharge from a lubricant which is located in a housing of an internal combustion engine, wherein the method comprises measuring a first lambda deviation by means of a lambda probe during a first air mass flow which is fed into an intake section of the internal combustion engine, measuring a second lambda deviation by means of the lambda probe during a second air mass flow which is fed into an intake section of the internal combustion engine and which differs from the first air mass flow, forming an actual comparison value from the measured first lambda deviation and the measured second lambda deviation, forming a setpoint comparison value from a first setpoint lambda deviation during the first air mass flow and a second setpoint lambda deviation during the second air mass flow, wherein the setpoint comparison value is indicative of the fuel discharge, and detecting the fuel discharge based on a comparison of the actual comparison value with the setpoint comparison value.

In a further embodiment, the first air mass flow is selected to be smaller than the second air mass flow, and the first setpoint lambda deviation is greater during the first air mass flow than the second setpoint lambda deviation during the second air mass flow.

In a further embodiment, the actual comparison value is formed from an actual difference between the first measured lambda deviation and the second measured lambda deviation, wherein the setpoint comparison value is formed from a setpoint difference between the first setpoint lambda deviation and the second setpoint lambda deviation, and wherein the setpoint difference between the first setpoint lambda deviation during the first mass flow and the second setpoint lambda deviation during the second mass flow is indicative of a characteristic mass flow of the fuel discharge, with the result that when the actual comparison value is compared with the setpoint comparison value the mass flow of the fuel discharge can be determined.

In a further embodiment, the first air mass flow and the second air mass flow are predefined by a control unit.

In a further embodiment, the first air mass flow and the second air mass flow are predefined by a user of the internal combustion engine.

In a further embodiment, the measurement of the first lambda deviation and the measurement of the second lambda deviation are carried out in an idling mode of the internal combustion engine.

Another embodiment provides a control device for an internal combustion engine of a motor vehicle, wherein the control device is configured to execute the method as disclosed above.

Another embodiment provides a computer program for detecting fuel discharge from a lubricant, which computer program is stored in non-transitory computer-readable media and executable by a processor to perform the method as disclosed above.

BRIEF DESCRIPTION OF THE DRAWINGS

FIG. 2 shows a flowchart with an example method according to an embodiment of the present invention; and FIG. 3 shows a schematic drawing of an internal combustion engine with an example controller according to an embodiment of the present invention.

DETAILED DESCRIPTION

Figure 1:
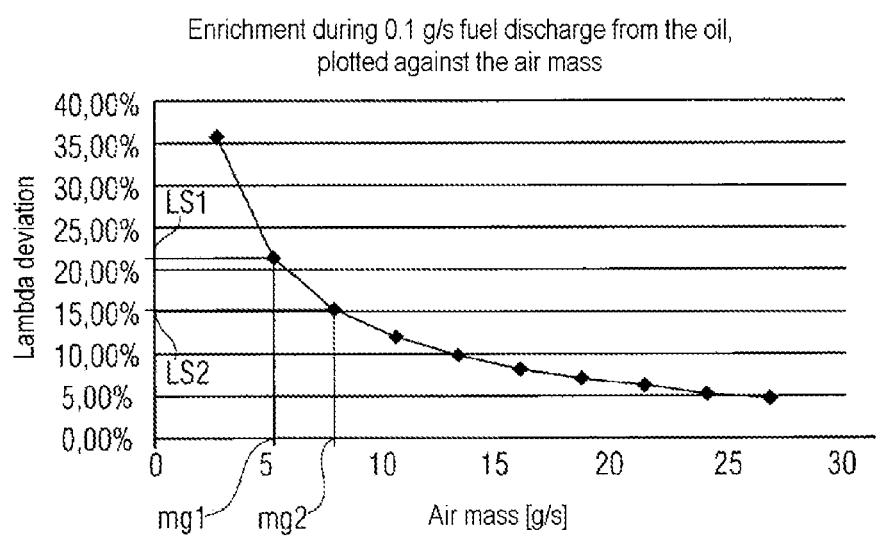
FIG. 1 shows a diagram with setpoint lambda deviations, calculated by way of example, for specific air masses according to an example embodiment of the present invention.

Embodiments of the present invention provide a simple and precise method for determining fuel discharge from a lubricant of an engine.

Some embodiments provide a method for detecting fuel discharge from a lubricant (for example engine oil) is described which is located in a housing (for example a crank casing) of an internal combustion engine (for example a spark-ignition engine). According to the method, a first lambda deviation of a lambda probe is measured during a first air mass flow which is fed into an intake section of the internal combustion engine. In addition, a second lambda deviation of the lambda probe is calculated during a second air mass flow which is fed into an intake section of the internal combustion engine. The first air mass flow differs from the second air mass flow.

An actual comparison value is formed from the measured first lambda deviation and the measured second lambda deviation. In addition, a setpoint comparison value is formed or calculated from a first setpoint lambda deviation during the first air mass flow and a second setpoint lambda deviation during the second air mass flow. The setpoint comparison value is indicative of fuel discharge from the lubricant. The fuel discharge is detected based on a comparison of the actual comparison value and of the setpoint comparison value. For example, fuel discharge is occurring when the actual comparison value corresponds to the setpoint comparison value.

According to a further embodiment, a control device for an internal combustion engine of a motor vehicle is described, wherein the control device is configured in such a way that the method described above can be executed.

The internal combustion engine is, in particular, a spark-ignition engine. The fuel which is used to operate the internal combustion engine can have proportions of petrol, diesel and/or ethanol.

The internal combustion engine has an intake section in which a mixture of fuel and air is made available. The fuel/air mixture is fed to the internal combustion engine from the intake section, which is formed, in particular, by means of an intake manifold. After the combustion of the fuel/air mixture in the internal combustion engine, the combustion exhaust gas is discharged from the internal combustion engine through an exhaust pipe. A lambda probe is arranged in such a way that the respective residual oxygen content can be measured in the combustion exhaust gas, in order to measure therefrom the ratio of combustion air to unburnt fuel. A $\lambda$ value is calculated as a function of the ratio of combustion air to the unburnt fuel.

The lambda value in the exhaust gas flow of the internal combustion engine specifies the ratio between air and unburnt fuel in comparison to a stochiometric mixture between air and fuel. If the lambda value $\lambda=1$ (is present in the case of a stochiometric mixture), precisely the quantity of air required to completely burn all of the fuel was present during the combustion. If more fuel is present, the fuel/air mixture during the combustion was too rich ($\lambda<1$). If excess air was present, the fuel/air mixture was too lean ($\lambda>1$) during the combustion.

Depending on the fuel used and on various engine parameters, the desired lambda value can be between 0.95 and 1.05 in order, for example, to achieve the highest power with, for example, minimum pollution.

The stochiometric mixture denotes the mass ratio of the proportion of air to the proportion of fuel at which all the fuel reacts or burns with all of the oxygen during combustion. In the case of petrol, the mass ratio is, for example, 14.7 parts of air to 1 part of petrol (14.7/1), whereas in the case of ethanol 9 parts of air are necessary for the combustion of 1 part of ethanol (9/1).

In some embodiments, a first lambda deviation is firstly measured by means of a lambda probe, and a second lambda deviation by means of a lambda probe for different air mass flows which are present in the intake section of the internal combustion engine.

In the present document a lambda deviation describes a percentage deviation of a measured lambda value from the value $\lambda=1$. In particular, a lambda deviation describes the percentage deviation from the lambda value $\lambda=1$ in the direction of a rich fuel/air mixture. If the lambda deviation is, for example, 5%, a measured lambda value of the lambda probe of 0.95 is present. If the lambda deviation is, for example, 10%, a measured lambda value of $\lambda=0.9$ is present.

In some embodiments, an actual comparison value is formed from the measured first and second lambda deviations. The actual comparison value is formed, for example, by forming a ratio between the first lambda deviation and the second lambda deviation (=first lambda deviation/second lambda deviation). In addition, the actual comparison value can be formed, for example, by forming a difference between the first lambda deviation and the second lambda deviation (=first lambda deviation−second lambda deviation).

In addition, in some embodiments a setpoint comparison value is formed between a first setpoint lambda deviation during the first air mass flow and a second setpoint lambda deviation during the second air mass flow. The setpoint comparison value is formed by the same calculation method (for example division or subtraction) as the actual comparison value. If, for example, the actual comparison value is formed by forming a ratio between the first lambda deviation and the second lambda deviation, the setpoint comparison value is also formed by forming a ratio between the first setpoint lambda deviation and the second setpoint lambda deviation. The same applies in the event of the actual comparison value being formed by forming a difference between the measured lambda deviations.

The first setpoint lambda deviation during the first air mass flow and the second setpoint lambda deviation during the second air mass flow are determined by means of a calculation model or determined by means of laboratory tests.

A setpoint lambda deviation can be calculated, for example, by means of the following formula:

$$\Delta\lambda = \frac{\frac{MFF_{Oil}}{MAF}}{\left(1 + \frac{\frac{MFF_{Oil}}{MAF}}{14.7}\right)}$$

where:
$\Delta\lambda = \lambda$ deviation, for example into the relatively rich region ($\lambda = 1 - \Delta\lambda$),
$MEF_{Oil}$ = mass flow (mass fuel flow) of the fuel from the lubricant,
MAF = mass flow (mass air flow) of the air in the intake section of the spark-ignition engine, and
14.7 = stochiometric fuel ratio (can vary for different fuels).

During the calculation of the setpoint lambda deviation by means of the above formula, operation of the internal combustion engine with $\lambda=1$ and a predefined mass flow ($MFF_{Oil}$ in gram/second) of the fuel discharge from the lubricant is predefined by means of the air mass in the intake section of the spark-ignition engine (MAF in gram/second). The calculation model will be explained in more detail in the figure which is described in more detail below.

A fuel discharge from the lubricant which is fed to the intake section brings about a correspondingly richer fuel/air mixture in the intake section. This richer fuel/air mixture is detected by the lambda probe after the combustion as a result of the unburnt excess fuel. In the event of a fuel discharge from the lubricant enriching the fuel/air mixture in the intake section, the lambda control will correspondingly react with a reduction in the injected fuel quantity. The extent to which this counter-control is effective depends, in particular, on the ratio of the fuel quantity discharged from the lubricant to the air mass throughput in the intake section.

Aspects of the invention is based on the realization that based on an air-mass-dependent behavior of the lambda deviation it is possible to infer that the enrichment of the fuel/air mixture involves an input of fuel which is outgased from the lubricant. Furthermore, by comparing the profile of the measured actual lambda deviation for various air mass flows in the intake section with a profile of the calculated setpoint lambda deviation for the air mass flows the quantity of discharged fuel from the lubricant can be determined.

In other words, a characteristic behavior of the lambda deviation with respect to different air mass flows in the intake section can be detected if fuel is input into the intake section from a lubricant. This characteristic behavior can be determined as described above.

If during the operation of the internal combustion engine the first lambda deviation is then measured during a first mass flow, and the second lambda deviation is measured during a second mass flow, and the measured lambda deviations (or actual comparison value) are compared with the corresponding setpoint lambda deviations (or setpoint comparison value), which were calculated for the same air mass flows, it is possible to infer that the corresponding measured lambda deviations are due to fuel discharge from the lubricating oil.

A simple measuring method is therefore made available for detecting fuel discharge from a lubricant. If such fuel discharge from the lubricant is detected, it can therefore be concluded from the reverse argument that the lambda deviations are based on some other fault. A fault diagnosis can therefore be avoided.

According to a further embodiment, the first air mass flow is selected to be smaller than the second air mass flow. In addition, the first setpoint lambda deviation is greater during the first air mass flow than the second setpoint lambda deviation during the second air mass flow. Aspects of the invention are based, in particular, on the realization that in the case of fuel discharge from the lubricant and in the case of corresponding inputting of fuel into the intake section during an increasing air mass flow through the intake section a smaller lambda deviation is brought about. The drop in the lambda deviation when there is an increase in the air mass flow is therefore characteristic of a specific quantity of fuel discharge from the lubricant.

According to a further embodiment, the actual comparison value is formed, for example, from an actual difference between the first measured lambda deviation and the second measured lambda deviation. The setpoint comparison value is formed from a setpoint difference between the first setpoint lambda deviation and the second setpoint lambda deviation. The setpoint difference between the first setpoint lambda deviation during the first mass flow and the second setpoint lambda deviation during the second mass flow is additionally indicative of a characteristic mass flow of the fuel discharge, with the result that when the actual comparison value, which is based on the actual difference, is compared with the setpoint comparison value, which is based on the setpoint difference, the mass flow or the quantity of the fuel discharge from the lubricant oil can be detected. In other words, by comparing the profile of the measured actual lambda deviation for various air mass flows with various profiles of the calculated setpoint lambda deviation, which are each indicative of different quantities of the fuel discharge for certain air mass flows, are compared. If the profile of the measured actual lambda deviations corresponds to a specific profile of setpoint lambda deviations, said profile being indicative of a specific quantity of fuel discharge from the lubricant, the quantity of fuel discharge from the lubricant can be determined from the reverse argument.

As a result, it is not only possible to generally infer the presence of fuel discharge from the lubricant, it is also possible to determine the quantity of fuel discharge from the lubricant.

According to a further embodiment, the first air mass flow and the second air mass flow are predefined by a control unit. The air mass flow which is conducted through the intake section is controlled, for example, by a throttle valve in the intake section. The control unit can, for example, control the throttle valve in order to selectively predefine a first air mass flow and a second air mass flow. The first lambda deviation and the second lambda deviation are correspondingly measured for the corresponding first air mass flow and second air mass flow. The control unit can predefine air mass flows independently and automatically, without intervention by a user, and initiate a measurement of the lambda deviations.

As an alternative to this, the first air mass flow and the second air mass flow are predefined by a user of the internal combustion engine. For example, the user can activate the accelerator pedal of a motor vehicle in which the internal combustion engine is installed, in order thereby to vary the air mass flow in the intake section. While the air mass flow changes, the first lambda deviation is measured during a first air mass flow, and the second lambda deviation is measured during a second air mass flow, in order thereby to determine the presence of outgasing of the fuel from the lubricant.

For example, in a vehicle having an automatic transmission it is proposed that in a neutral phase (shift position N, idling) the first lambda deviation is measured for the first air mass flow, and that after the engagement of the transmission (from shift position N to D of the transmission) the second lambda deviation is measured for the second air mass flow which is present in this operating state.

In particular, the measurement of the first lambda deviation and the measurement of the second lambda deviation can be carried out in an idling mode of the internal combustion engine. In an idling mode, the internal combustion engine is decoupled from a transmission of the motor vehicle. In the idling mode, an extremely low air mass flow is conducted through the intake section. As can be seen in the figure below, the lambda deviation during small air mass flows is highest in the case of fuel discharge from the lubricant, with the result that high lambda deviations can be measured between two small air mass flows. As a result, good measurement results and better statements about the presence of fuel discharge from the lubricant can be made.

By means of the control unit, the air mass, for example in the idling mode, is increased actively (without intervention by the user) or passively (during a change in the air mass flow by the user). For example, during the building up of a torque reserve the control unit can initiate a measurement of the lambda deviations.

In the described method, the lambda deviation is not evaluated for one and the same air mass flow but rather two lambda deviations are measured for two different air mass flows. This produces the advantage that lambda deviations which are caused, for example, by faulty injection systems or air mass-detection faults cannot be incorrectly attributed to fuel discharge from the lubricant, and vice-versa.

The control unit can have, for example, a programmable process.

In addition, the control unit can have a database in which, for example, data for the specific setpoint lambda deviations during specific air mass flows and/or for specific mass flows of the fuel discharge from the lubricant are stored, it being possible to call said data from the processor. In addition, for example the control coordinates of the throttle valve or the ignition times of the internal combustion engine can be stored as parameters in the database. In addition, the control unit can automatically initiate the method described above if suitable measuring conditions such as, for example, idling of the internal combustion engine are present.

Other embodiments provide a computer program for detecting fuel discharge from a lubricant is described. The computer program is configured to carry out the method described above when the computer program is executed by a processor.

According to this document, the naming of such a computer program is equivalent to the term of a program element, of a computer program product and/or of a non-transitory computer-readable medium which contains instructions for controlling a computer system, in order to coordinate the method of operation of a system or of a method in a suitable way, in order to achieve the effects linked to the disclosed method.

The computer program can be implemented as computer-readable instruction code in any suitable programming language such as, for example, in JAVA, C++ etc. The computer program can be stored on a computer-readable storage medium (CD-Rom, DVD, Blu-ray disk, replaceable disk drive, volatile or non-volatile memory, built-in memory/processor etc). The instruction code can program a computer or other programmable devices such as, in particular, a control unit or the control device described above for an internal combustion engine of a motor vehicle, in such a way that the desired functions are executed. In addition, the computer program can be made available in a network such as, for example, the internet, from which it can be downloaded by a user when required.

Embodiments can be implemented by means of a computer program, i.e., software, as well as by means of one or more special electric circuits, i.e. in hardware or in any desired hybrid form, i.e. by means of software components and hardware components.

It is to be noted that the embodiments described here merely constitute a restricted selection of possible embodiment variants. It is therefore possible to combine the features of individual embodiments with one another in a suitable way, with the result that a person skilled in the art considers the embodiment variants which are explicit here as publically disclosing a plurality of different embodiments.

FIG. 1 shows characteristic lambda deviations during specific air mass flows. The illustrated lambda deviations are characteristic of enrichment of the fuel/air mixture in the intake section of an internal combustion engine when the fuel/air mixture has been input during a mass flow of 0.1 g/s (grams per second) of fuel discharge from the lubricant into the intake section.

In other words, during the production of the diagram from the figure, fuel discharge from the lubricant of 0.1 g/s is assumed, which fuel discharge is correspondingly fed into the fuel/air mixture in the intake section. In the case of enrichment of 0.1 g/s, in a first air mass flow ms1 of approximately 5 g/s a first setpoint lambda deviation Ls1 of approximately 22% occurs. Correspondingly, in the case of a second air mass flow ms2 of approximately 8 g/s a second setpoint lambda deviation Ls2 of approximately 15% occurs. The setpoint values of the diagram from the figure are calculated with the formula for $\Delta\lambda$ which is specified further above.

According to the method disclosed herein, a setpoint comparison value is formed from the measured setpoint lambda deviations Ls1 and Ls2 (for example by forming a difference). Corresponding characteristic profiles of the lambda deviation plotted against air mass flows can be calculated for a plurality of different magnitudes of fuel discharges from the lubricant plotted against the air mass.

As explained at the beginning, the figure merely represents exemplary lambda deviations plotted against various air masses for fuel discharge of 0.1 g/s. The plurality of different characteristic lambda deviation profiles plotted against the air mass for various fuel discharges can be stored in a database.

During operation of the internal combustion engine, during a first air mass flow ms1 a first actual lambda deviation is measured, and during a second air mass flow ms2 a second actual lambda deviation is measured. Subsequently, an actual comparison value is formed from the first actual lambda deviation and the second actual lambda deviation. If the actual comparison value corresponds to a setpoint comparison value for the corresponding air mass flows ms1 and ms2, it is possible to infer that the measured actual lambda deviations are caused by enrichment of the fuel/air mixture in the intake section with fuel discharge from the lubricant. By comparing the gradient of the actual lambda deviations and the setpoint lambda deviations Ls1, Ls2 for the various air mass flows ms1, ms2 it is possible to infer, for example, the level of the fuel discharge from the lubricant.

In order to detect the most precise profile of the lambda deviation as possible during certain air mass flows, it is additionally possible to measure a plurality of actual lambda deviations during a plurality of different air mass flows.

In addition it is to be noted that "comprising" does not exclude any other elements or steps and "a" or "an" does not exclude a plurality. In addition it is to be noted that features or steps which have been described with reference to one of the above exemplary embodiments can also be used in combination with other features or steps of other exemplary embodiments described above.

LIST OF SYMBOLS

Ls1 First setpoint lambda deviation
Ls2 Second setpoint lambda deviation
ms1 First air mass flow
ms2 Second air mass flow

What is claimed is:

1. A method for controlling an injected fuel quantity for an internal combustion engine based on detection of fuel discharge from a lubricant located in a housing of the internal combustion engine, the method comprising:
    measuring a first lambda deviation by a lambda probe during a first air mass flow fed into an intake section of the internal combustion engine,
    measuring a second lambda deviation by the lambda probe during a second air mass flow fed into the intake section of the internal combustion engine, the second air mass flow differing from the first air mass flow,
    determining an actual comparison value from the measured first lambda deviation and the measured second lambda deviation,
    determining a setpoint comparison value from a first setpoint lambda deviation during the first air mass flow and a second setpoint lambda deviation during the second air mass flow, wherein the setpoint comparison value is indicative of the fuel discharge,
    detecting the fuel discharge based on a comparison of the actual comparison value with the setpoint comparison value,
    wherein the actual comparison value is determined from an actual difference between the first measured lambda deviation and the second measured lambda deviation,
    the setpoint comparison value is determined from a setpoint difference between the first setpoint lambda deviation and the second setpoint lambda deviation, and
    the setpoint difference between the first setpoint lambda deviation during the first mass flow and the second setpoint lambda deviation during the second mass flow is indicative of a characteristic mass flow of the fuel discharge, such that the fuel discharge is determinable from the comparison of the actual comparison value with the setpoint comparison value, and
    adjusting the injected fuel quantity based on the detected fuel discharge from the lubricant.

2. The method of claim 1, wherein:
    the first air mass flow is selected to be smaller than the second air mass flow, and
    the first setpoint lambda deviation is greater during the first air mass flow than the second setpoint lambda deviation during the second air mass flow.

3. The method of claim 1, comprising predefining, by a control unit, the first air mass flow and the second air mass flow.

4. The method of claim 1, wherein the first air mass flow and the second air mass flow are predefined by a user of the internal combustion engine.

5. The method of claim 1, comprising performing the measurement of the first lambda deviation and the measurement of the second lambda deviation in an idling mode of the internal combustion engine.

6. A control device for an internal combustion engine of a motor vehicle, wherein the control device comprises:
    a processor; and
    computer instructions stored in non-transitory computer-readable media and executable by the processor to control an injected fuel quantity based on detection of fuel discharge from a lubricant located in a housing of the internal combustion engine by a process including:
        measuring a first lambda deviation by a lambda probe during a first air mass flow fed into an intake section of the internal combustion engine,
        measuring a second lambda deviation by the lambda probe during a second air mass flow fed into the intake section of the internal combustion engine, the second air mass flow differing from the first air mass flow,
        determining an actual comparison value from the measured first lambda deviation and the measured second lambda deviation,
        determining a setpoint comparison value from a first setpoint lambda deviation during the first air mass flow and a second setpoint lambda deviation during the second air mass flow, wherein the setpoint comparison value is indicative of the fuel discharge,
        detecting the fuel discharge based on a comparison of the actual comparison value with the setpoint comparison value,
        determining the actual comparison value from an actual difference between the first measured lambda deviation and the second measured lambda deviation,
        determining the setpoint comparison value from a setpoint difference between the first setpoint lambda deviation and the second setpoint lambda deviation,
        wherein the setpoint difference between the first setpoint lambda deviation during the first mass flow and the second setpoint lambda deviation during the second mass flow is indicative of a characteristic mass flow of the fuel discharge, such that the fuel discharge is determinable from the comparison of the actual comparison value with the setpoint comparison value, and
        adjusting the injected fuel quantity based on the detected fuel discharge from the lubricant.

7. The control device of claim 6, wherein:
    the first air mass flow is selected to be smaller than the second air mass flow, and
    the first setpoint lambda deviation is greater during the first air mass flow than the second setpoint lambda deviation during the second air mass flow.

8. The control device of claim 6, wherein the first air mass flow and the second air mass flow are predefined by the control device.

9. The control device of claim 6, wherein the first air mass flow and the second air mass flow are predefined by a user of the internal combustion engine.

10. The control device of claim 6, wherein the computer instructions are executable to perform the measurement of the first lambda deviation and the measurement of the second lambda deviation in an idling mode of the internal combustion engine.

\* \* \* \* \*